(12) United States Patent
Fujieda et al.

(10) Patent No.: US 6,467,907 B1
(45) Date of Patent: Oct. 22, 2002

(54) APPARATUS FOR DETERMINING AN AMOUNT OF CORNEAL ABLATION AND SURGICAL APPARATUS FOR A CORNEA

(75) Inventors: Masanao Fujieda, Toyohashi; Yokinobu Ban, Nishio; Masahiro Oyaizu, Gamagori, all of (JP)

(73) Assignee: Nidek Co., Ltd., Aichi (JP)

(*) Notice: Subject to any disclaimer, the term of this patent is extended or adjusted under 35 U.S.C. 154(b) by 0 days.

(21) Appl. No.: 09/744,909

(22) PCT Filed: Aug. 3, 2000

(86) PCT No.: PCT/JP00/05250

§ 371 (c)(1),
(2), (4) Date: Jan. 31, 2001

(87) PCT Pub. No.: WO01/28479

PCT Pub. Date: Apr. 26, 2001

(30) Foreign Application Priority Data

Oct. 21, 1999 (JP) ............................................. 11-300148

(51) Int. Cl.$^7$ ................................................. A61B 3/10
(52) U.S. Cl. ........................................... 351/212; 606/5
(58) Field of Search ................................. 351/205, 211, 351/212; 606/4, 5, 10, 13, 166

(56) References Cited

U.S. PATENT DOCUMENTS

| | | |
|---|---|---|
| 4,878,750 A | 11/1989 | Sekiguchi |
| 5,460,627 A | 10/1995 | O'Donnell, Jr. |
| 5,500,697 A | 3/1996 | Fujieda |
| 5,800,424 A | 9/1998 | Sumiya |
| 5,841,511 A | 11/1998 | D'Souza et al. |
| 5,906,608 A | 5/1999 | Sumiya et al. |
| 5,907,388 A | 5/1999 | Fujieda |
| 6,033,075 A | 3/2000 | Fujieda et al. |
| 2001/5411501 | * 5/1995 | Ioptek .............................. 606/4 |
| 2001/6280435 | * 8/2001 | Odrich et al. ................... 606/5 |

FOREIGN PATENT DOCUMENTS

| | | |
|---|---|---|
| EP | 0 811 352 | 12/1997 |
| EP | 0 911 001 | 4/1999 |
| EP | 0 983 757 | 9/1999 |
| JP | 3-51166 | 8/1991 |
| JP | 6-226471 | 8/1994 |
| WO | WO 92/01419 | 2/1992 |

* cited by examiner

*Primary Examiner*—George Manuel
(74) *Attorney, Agent, or Firm*—Finnegan, Henderson, Farabow, Garrett & Dunner, L.L.P.

(57) ABSTRACT

The purpose of the present invention is to provide an apparatus for determining an amount of corneal ablation, which can calculates an amount of corneal ablation in order to perform an operation for correcting ametropia adequately, based on a corneal shape and/or an eye refractive power. Another object of the present invention is to provide a surgical apparatus for a cornea, by which the surgical operation can be performed efficiently based on the obtained amount of corneal ablation. The apparatus for determining an amount of corneal ablation, based on which surgical operation for correcting ametropia is performed, the apparatus comprises a first input unit (53) for inputting data of a pre-operative corneal shape of a patient's eye; a second input unit (52, 53, 54) for inputting data of a post-operative corneal shape of the eye, to be estimated (to be a target for correcting); an ablation amount calculating unit (54) for calculating data of a corneal ablation amount of the eye, in a manner of calculating data of an ablation amount in a symmetric component and data of an ablation amount in an asymmetric component separately and respectively, based on the data inputted by the first input unit and the second input unit; and an output unit (56, 59a, 59b) for outputting results calculated by the ablation amount calculating unit.

15 Claims, 11 Drawing Sheets

(a)

(b)

Calculated corneal refractive power based on the corneal shape measurement

Calculated (Measured) eye refractive power based on the eye refractive power measurement (a)

(b)

(a)

(b)

US 6,467,907 B1

APPARATUS FOR DETERMINING AN AMOUNT OF CORNEAL ABLATION AND SURGICAL APPARATUS FOR A CORNEA

TECHNICAL FIELD

The present invention relates to an apparatus for determining an amount of corneal ablation and a surgical apparatus for a cornea, and more particularly, to the apparatus utilized for correcting ametropia in a manner of ablating a corneal surface and varying its shape.

BACKGROUND ART

It is known for surgery operation, by which ametropia of an eye is corrected by a process of ablating a corneal surface (corneal stroma and the like) with a laser beam then varying its shape. In the surgical operation, both of a corneal shape (a corneal surface shape) and a refractive power of the eye to be operated (a patient's eye) are obtained, based on which, an amount of corneal ablation necessary for correction is calculated and found. In the past, procedures for calculating an amount of corneal ablation is conducted as following.

Firstly, a corneal surface of the eye to be operated is assumed as a spherical surface or a toric surface, with this assumption, a corneal shape is estimated based on an average of a pre-operative corneal radius of curvature obtained by a corneal shape measurement. Then, an amount of corneal ablation is calculated on the assumption that a post-operative corneal shape is also to be in a shape of a spherical surface or a toric surface. This calculation is based on the values S (a spherical power), C (a cylindrical power) and A (an astigmatic axial angle) found by a subjective eye refractive power measurement and/or an objective eye refractive power measurement.

However, a cornea of a human eye does not always have a symmetric shape, such as a spherical surface, a toric surface or the like. Thus, there are some cases that a corneal shape is in an asymmetric shape such that a corneal surface shape is different in part due to irregular astigmatism or the like. In order to perform an operation for correcting ametropia adequately, it is insufficient to calculate the ablation data (i.e., data of a corneal ablation amount) composed only of a symmetric shape (i.e., a symmetric component), such as a spherical surface or a toric surface.

The present invention has been made in view of the above circumstances and has an object to overcome the above problems and to provide an apparatus for determining an amount of corneal ablation, which can calculates an amount of corneal ablation in order to perform an operation for correcting ametropia adequately, based on a corneal shape and/or an eye refractive power.

Another object of the present invention is to provide a surgical apparatus for a cornea, by which the surgical operation can be performed efficiently based on the obtained amount of corneal ablation.

DISCLOSURE OF INVENTION

To achieve the objects and in accordance with the purpose of the present invention, as embodied and broadly described herein, the present invention comprises below mentioned construction.

An apparatus for determining an amount of corneal ablation, based on which surgical operation for correcting ametropia is performed, according to claim 1, the apparatus comprises a first input unit for inputting data of a pre-operative corneal shape of a patient's eye; a second input unit for inputting data of a post-operative corneal shape of the eye, to be estimated; an ablation amount calculating unit for calculating data of a corneal ablation amount of the eye, in a manner of calculating data of an ablation amount in a symmetric component and data of an ablation amount in an asymmetric component separately and respectively, based on the data inputted by the first input unit and the second input unit; and an output unit for outputting results calculated by the ablation amount calculating unit.

In this case, as according to claim 2, the output unit may preferably comprise a display unit for displaying the results calculated by the ablation amount calculating unit, graphically.

In this case, furthermore, as according to claim 3, the output unit may preferably comprise a sending unit for sending the results calculated by the ablation amount calculating unit, to a surgical apparatus for a cornea.

In this case, furthermore, as according to claim 4, the ablation amount calculating unit may satisfactorily calculate at least one data selected from the group consisting of a spherical component, a non-spherical component, and a cylindrical component, for use as the data of the ablation amount in the symmetric component.

Furthermore, as according to claim 5, the apparatus according to claim 1, may further comprise a corneal shape measuring unit for measuring distribution data of a pre-operative corneal radius of curvature of the eye; in which the first input unit may satisfactorily input pre-operative distribution data measured by the corneal shape measuring unit into the ablation amount calculating unit.

Furthermore, as according to claim 6, the apparatus according to claim 1, may further comprise a corneal shape measuring unit for measuring distribution data of a pre-operative corneal radius of curvature of the eye; an eye refractive power measuring unit for measuring distribution data of a pre-operative refractive power of the eye; a corneal shape calculating unit for calculating distribution data of an equivalent emmetropia corneal refractive power of the eye based on pre-operative distribution data measured by the corneal shape measuring unit and pre-operative distribution data measured by the eye refractive power measuring unit, subsequently, calculating the distribution data of a post-operative corneal radius of curvatur of the eye, to be estimated, based on the obtained distribution data of an equivalent emmetropia corneal refractive power; in which the first input unit may satisfactorily input pre-operative distribution data measured by the corneal shape measuring unit into the ablation amount calculating unit, and the second input unit may satisfactorily input pre-operative distribution data measured by the corneal shape calculating unit into the ablation amount calculating unit.

In this case, as according to claim 7, the corneal shape calculating unit may preferably calculate the distribution data of a corneal refractive power based on distribution data of the corneal radius of curvature measured by the corneal shape measuring unit, subsequently, calculating the distribution data of the equivalent emmetropia corneal refractive power based on the obtained distribution data of the corneal refractive power and the distribution data of the eye refractive power measured by the eye refractive power measuring unit; and the output unit may preferably include a display unit for displaying graphically at least one distribution data selected from the group consisting of the distribution data of the corneal refractive power, the distribution data of the eye refractive power and the distribution data of the equivalent emmetropia corneal refractive power.

Furthermore, as according to claim 8, the apparatus according to claim 1, may further comprise a correcting-refractive power input unit for inputting data of a correcting-refractive power of the patient's eye; and a corneal shape calculating unit for calculating the data of a post-operative corneal shape, to be estimated, based on the inputted data of the correcting-refractive power; in which the second input unit may preferably input the results calculated by the corneal shape calculating unit into the ablation amount calculating unit.

Furthermore, as according to claim 9, the apparatus according to claim 1, at least one between the first input unit and the second input unit may satisfactorily comprise an input unit with which an operator inputs data.

A surgical apparatus for a cornea, which corrects ametropia by ablating a cornea of a patient's eye with a laser beam, according to claim 10, the apparatus comprises a first input unit for inputting data of a pre-operative corneal shape of a patient's eye; a second input unit for inputting data of a post-operative corneal shape of the eye, to be estimated; an ablation amount calculating unit for calculating data of a corneal ablation amount of the eye, in a manner of calculating data of an ablation amount in a symmetric component and data of an ablation amount in an asymmetric component separately and respectively, based on the data inputted by the first input unit and the second input unit; a first ablation unit for ablating the cornea, based on the obtained data of the ablation amount in the symmetric component; and a second ablation unit for ablating the cornea, based on the obtained data of the ablation amount in the asymmetric component.

In this case, as according to claim 11, the first ablation unit may satisfactorily comprise an irradiating optical system for irradiating the cornea with the laser beam from a laser source; and the second ablation unit may satisfactorily share the irradiating optical system with the first ablation unit.

In this case, furthermore, as according to claim 12, the second ablation unit may satisfactorily comprise a beam dividing unit for dividing the laser beam, the beam dividing unit being disposed on a light path of the irradiating optical system.

An apparatus for determining an amount of corneal ablation, based on which surgical operation for correcting ametropia is performed, as according to claim 13, the apparatus comprises a corneal shape measuring unit for measuring distribution data of a corneal radius of curvature of a patient's eye; an eye refractive power measuring unit for measuring distribution data of an eye refractive power of the eye; a corneal shape calculating unit for calculating distribution data of an equivalent emmetropia corneal refractive power of the eye based on pre-operative distribution data measured by the corneal shape measuring unit and pre-operative distribution data measured by the eye refractive power measuring unit, subsequently, calculating distribution data of a post-operative corneal radius of curvature of the eye, to be estimated, based on the obtained distribution data of the equivalent emmetropia corneal refractive power; an ablation amount calculating unit for calculating data of a corneal ablation amount of the eye, in a manner of calculating data of an ablation amount in a symmetric component and data of an ablation amount in an asymmetric component separately and respectively, based on the results measured by the corneal shape measuring unit and the results calculated by the corneal shape calculating unit; and an output unit for outputting results calculated by the ablation amount calculating unit.

In this case, as according to claim 14, the corneal shape calculating unit may satisfactorily calculate distribution data of a corneal refractive power based on the distribution data of the corneal radius of curvature measured by the corneal shape measuring unit, subsequently, calculate the distribution data of the equivalent emmetropia corneal refractive power based on the obtained distribution data of the corneal refractive power and the distribution data of the eye refractive power measured by the eye refractive power measuring unit; and the output unit may satisfactorily include a display unit for displaying graphically at least one datum selected from the group consisting of the distribution data of the corneal refractive power, the distribution data of the eye refractive power, the distribution data of the equivalent emmetropia corneal refractive power, data of a total ablation amount, data of the ablation amount in the symmetric component and data of the ablation amount in the asymmetric component.

In this case, furthermore, as according to claim 15, the output unit may preferably comprise a sending unit for sending the results calculated by the ablation amount calculating unit, to a surgical apparatus for a cornea. dr

BEST MODE FOR CARRYING OUT THE INVENTION

Figure 1:
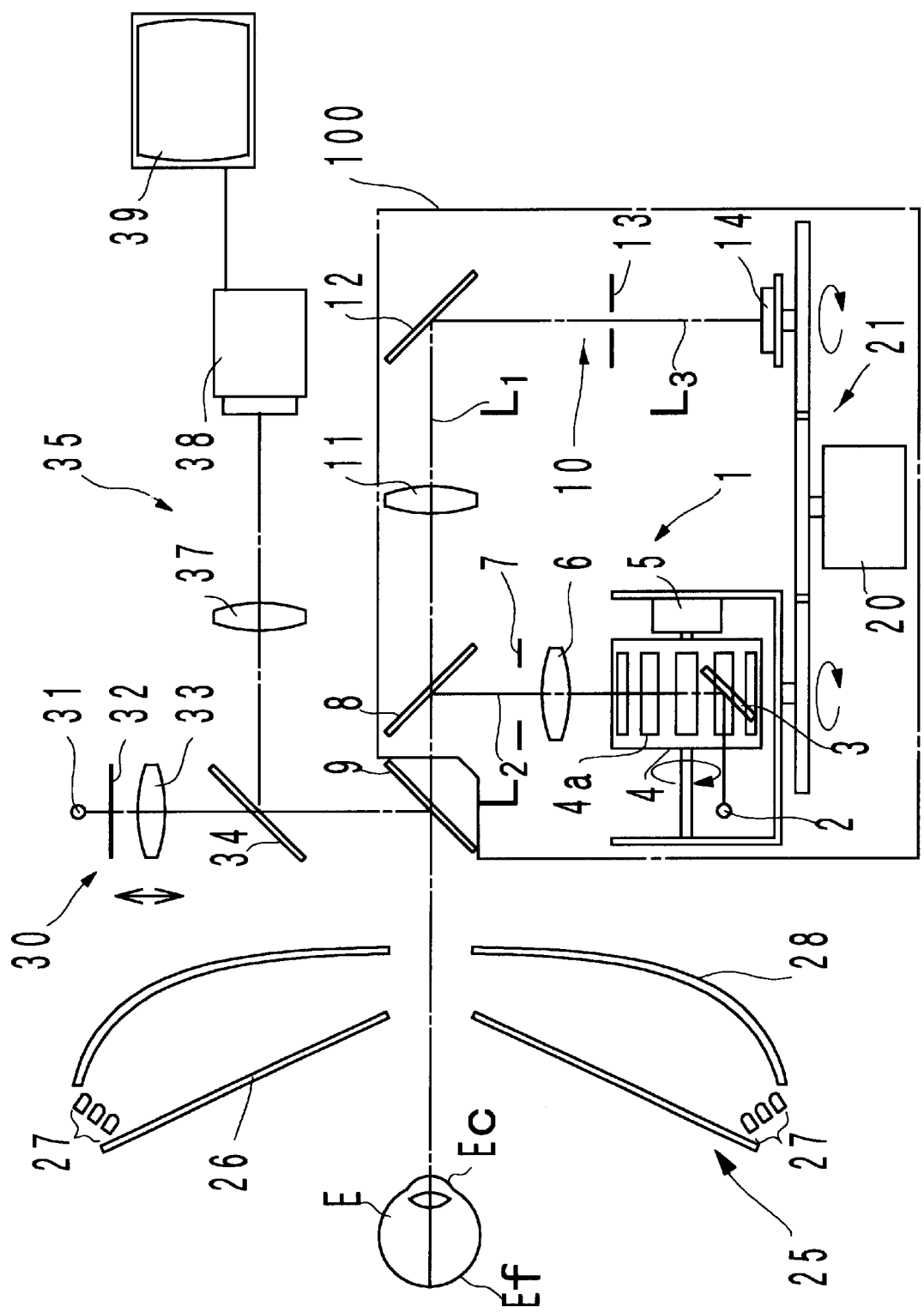
FIG. 1 is a view showing a schematic configuration of an optical system in the apparatus for determining an amount of corneal ablation of the preferred embodiment of the present invention.

A detailed description of one preferred embodiment of the present invention will now be given referring to the accompanying drawings. FIG. 1 is a view showing a schematic configuration of an optical system in the apparatus for determining an amount of corneal ablation of the preferred embodiment of the present invention. The optical system is roughly divided into an eye refractive power measuring optical system, a fixation target projecting optical system and a corneal radius of curvature measuring optical system.

(Eye Refractive Power Measuring Optical System)

The eye refractive power measuring optical system 100 includes a slit-light projecting optical system 1 and a slit-image detecting optical system 10. A light within a range of near infrared rays from a light source 2 of the slit-light projecting optical system 1 is reflected by a mirror 3, then illuminating a slit aperture 4a of a rotation sector 4. Driven by a motor 5, the rotation sector 4 rotates. A slit-light, scanned by a rotation of the sector 4, passes through a projecting lens 6 and a limit diaphragm 7, then being reflected by a beam splitter 8. The slit-light then transmits a beam splitter 9, then converging in the vicinity of a cornea Ec of a patient's eye E and being projected onto a fundus Ef thereof. The light source 2 is disposed at the conjugate position with the vicinity of the cornea Ec with respect to the projecting lens 6.

Figure 2:
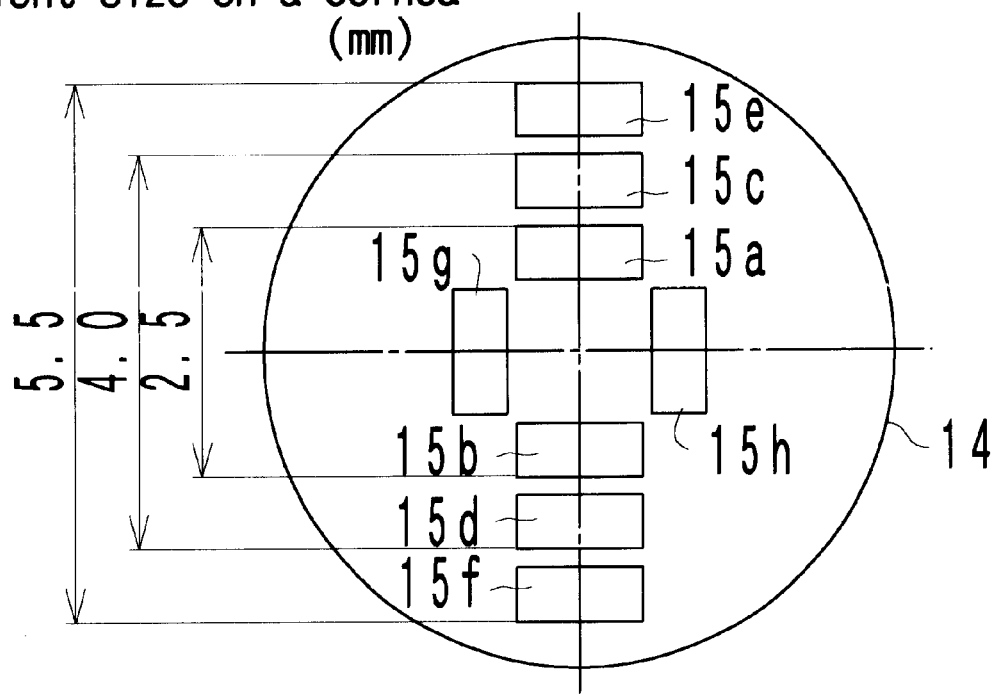
FIG. 2 is a view showing an arrangement of photodetectors provided for a photo-receiving part.

The detecting optical system 10 is provided with a photo-receiving lens 11 and a mirror 12, arranged on the principal optical axis L1, and a diaphragm 13 and a photo-receiving part 14, arranged on the optical axis L3. Where, the optical axis L3 is formed by reflection of the mirror 12. The diaphragm 13 is disposed at the back focal point of the lens 11 via the mirror 12 (i.e., at the conjugate position with a fundus of the eye having emmetropia). As shown in FIG. 2, eight photo-detectors 15a–15h are disposed on the surface of the photo-receiving part 14 so as to be at approximately the conjugate positions with the cornea Ec with respect to the lens 11. Six photo-detectors 15a–15f out of eight photo-detectors 15a–15h are disposed on the line passing through the center (i.e., the optical axis L3) of the photo-receiving surface, so as to make pairs, 15a with 15b, 15c with 15d, and 15e with 15f. Respective pairs are disposed so as to be symmetric with respect to the center of the photo-receiving surface. The configuration distance of these three pairs is set so as to detect a refractive power corresponding to respective positions in the meridian direction of the cornea Ec (in FIG. 2, it is shown as an equivalent size on a cornea). In contrast, the photo-detectors 15g and 15h are positioned on the line perpendicular to the line on which the photo-detectors 15a–15f are disposed, with the center at the optical axis L3, so as to be symmetric with respect to the center.

In the measuring optical system 100 having above-described construction, a rotation mechanism 21 comprising a motor 20, a gear and the like rotates the components of the projecting optical system 1, such as the light source 2, the mirror 3, the sector 4 and the motor 5, on the optical axis L2, and also rotates the photo-receiving part 14 on the optical axis L3 with making the rotations synchronized to each other. In the preferred embodiment, the photo-detectors 15a–15f are disposed in the direction perpendicularly intersecting the long side of the slit-light (image) received by the photo-receiving part 14, in the case that a slit-light is scanned on a fundus of the eye having hyperopia or myopia exclusive of astigmatism.

(Fixation Target Projecting Optical System)

30 is a fixation target projecting optical system, 31 is a visible light source, 32 is a fixation target and 33 is a projecting lens. The lens 33 moves toward the optical axis, thereby fogging the eye E. 34 is a beam splitter which makes an optical axis of the observation optical system coaxial. The light source 31 illuminates the fixation target 32, from which the light passes through the lens 33 and the beam splitter 34, then being reflected by the beam splitter 9, thereby reaching to the eye E. Accordingly, the eye E can be fixed to the fixation target 32.

(Corneal Radius of Curvature Measuring Optical System)

A corneal radius of curvature measuring optical system includes a target projecting optical system 25 for measuring a radius of curvature and a target image detecting optical system 35 for measuring a radius of curvature. The projecting optical system 25 has below mentioned configuration. 26 is a conic placido-plate provided with an aperture in the center thereof. On the placido-plate, there is formed ring patterns having a numerous light passing part and light blocking part on concentric circles with the center at the optical axis L1. 27 is a plurality of illumination light sources, such as LED or the like, the illumination light from the light source 27 is reflected by a reflecting plate 28, so as to illuminate the placido-plate 26 from behind almost evenly. The light having a ring pattern, passed through the light passing parts of the placido-plate 26, is projected onto the cornea Ec, and forms the ring pattern (placido-ring) image on the cornea Ec.

The detecting optical system 35 includes the beam splitter 9, the beam splitter 34, a photographing lens 37 and a CCD camera 38. A light of the ring pattern image formed on the cornea Ec is reflected by the beam splitter 9 and the beam splitter 34 in succession, then enters into the photographing elements of the camera 38 by the lens 37 (i.e., the image is received). In addition, the detecting optical system 35 also acts as an observation optical system. Therefore, a light of an anterior portion image of the eye E illuminated by an illumination light source for an anterior portion of an eyeball, not shown, enters into the photographing elements of the camera 38 (i.e., the image is received). TV monitor 39 displays the photographed anterior portion image of the eye and the ring pattern image formed on the cornea Ec.

Figure 3:
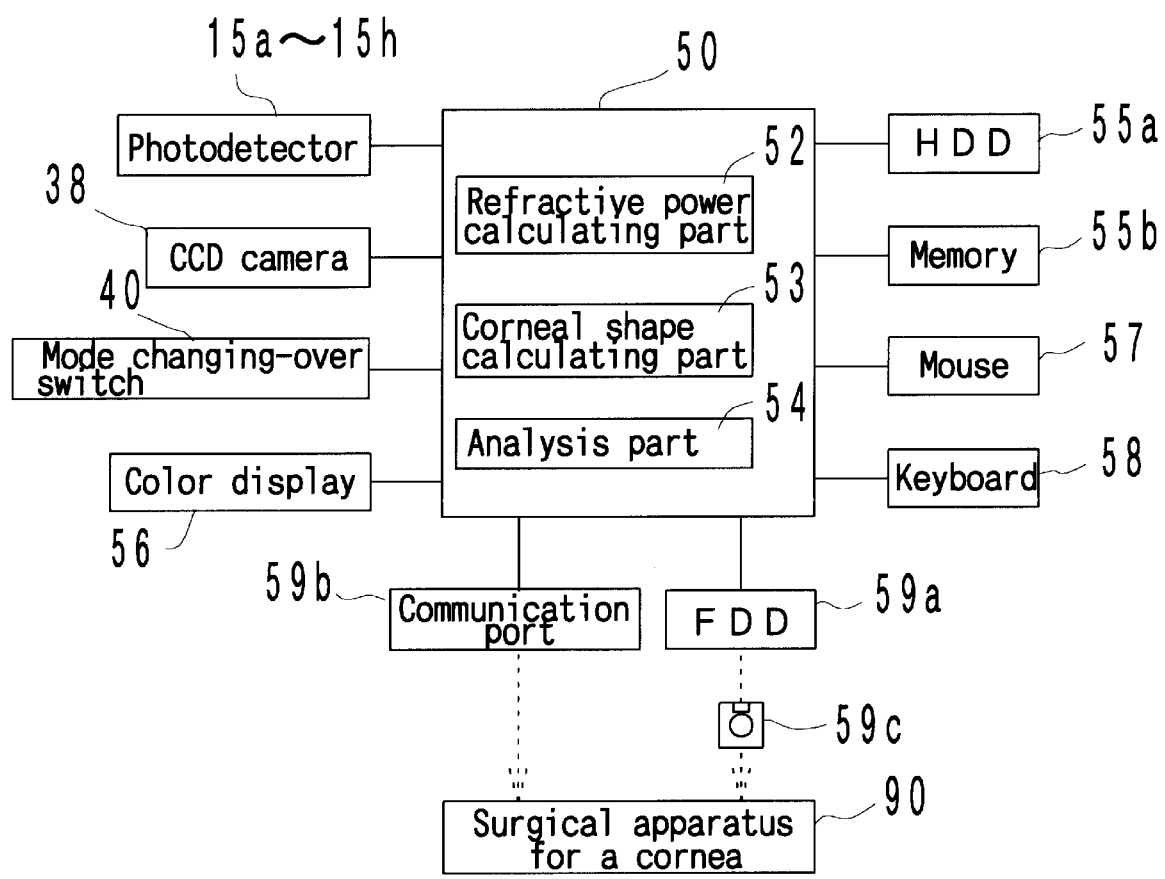
FIG. 3 is a view showing a schematic construction of a control system in the apparatus for determining an amount of corneal ablation of the preferred embodiment of the present invention.

Next, the operation of the apparatus having above mentioned architecture consistent with the present invention will be described hereinafter with referring to the block diagram of the control system shown in FIG. 3. Firstly, the measurement of a corneal radius of curvature (a corneal shape measurement) and the measurement of an eye refractive power will be described.

In the case of measuring a corneal radius of curvature, the operator selects the mode for measuring a corneal radius of curvature by using a mode changing-over switch 40. The operator performs alignment with observing the image of the anterior portion of the eye E displayed on the monitor 39, which is illuminated by the anterior portion illumination light source. (A well known manner can be used for the alignment. The manner is such that a target for positional adjustment is projected on the cornea Ec, then a corneal reflecting luminous point and a reticle are made to have the given relationship.) After completing alignment, the operator pushes a start switch for the measurement, not shown, thereby a trigger signal being generated, responding to which, the measurement is made to be started.

A corneal shape calculating part 53 detects an edge of an image of ring patterns by processing an image photographed by the camera 38. Then, the calculating part 53 calculates a corneal radius of curvature by obtaining each edge position relative to a vertex of the cornea Ec at intervals of a given angle (1°).

Figure 4:
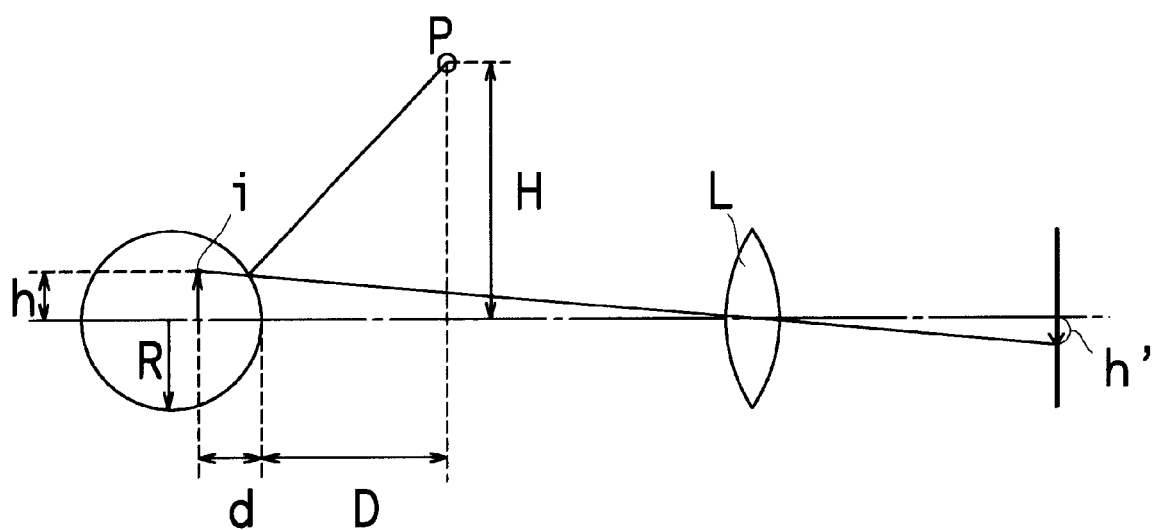
FIG. 4 is a view for illustrating a method of calculating a corneal radius of curvature.

The calculation for obtaining a corneal radius of curvature can be carried out as following. As shown in FIG. 4, the detected image height is defined as h' at the time when an image i due to the corneal convex surface of the light source P at the distance D on the optical axis and the height H from the cornea is formed on the two-dimensional detecting plane by the lens L. The magnification of the optical system of the apparatus is defined as m. The corneal radius of curvature R is given by following expression:

$$R=(2D/H)\ mh'$$

It is also possible to adapt a method of calculating a corneal radius of curvature as following. The corneal radius of curvature of the region where the j-th ring is projected onto the cornea is defined as Rj. The proportional constant which is determined by the height of the j-th ring, the distance up to the eye E and the photographing magnification, is defined as Kj. The image height on the photographing plane is defined as hj. Under the definition, the relationship expression as identified above is given by following expression:

$$Rj=kj\cdot hj$$

Where, if a plurality of model eyes having known different corneal radius of curvature which cover the measurement range is measured in advance, then the proportional constant Kj is obtained as an intrinsic value for the apparatus. Therefore, if the constant Kj is read out and utilized for calculation at the time of measuring, then the distribution of the corneal radius of curvature is obtained in extremely short time. (The details of this calculation, see U.S. Pat. No. 5,500,697 corresponding to the Japanese Patent Publication Laid-Open No. HEI 7(1995)-124113, or the like.) The obtained distribution data of the corneal radius of curvature is stored in a memory 55b.

A surgical apparatus for a cornea is used on the assumption that a pupil center is defined as an origin position of an eye, but, in general, a corneal vertex disagrees with a pupil center, so the positional relationship between a corneal shape (a corneal center or the like) and a pupil center should be found in advance. In view of this point, based on the anterior portion image photographed by the camera 38, a pupil center is defined as an intersecting point defined by following first and second lines: the first line is passing through a center between two points and extending in a perpendicular direction (the two points are respectively on opposite edges of a pupil, the points on edges are the intersecting points with a horizontal line passing through approximately a center of an pupil) and the second line is passing through a center between two points and extending in a horizontal direction (the two points are respectively on opposite edges of a pupil, the points on edges are intersecting points with a perpendicular line passing through approximately a center of a pupil). The method for definition of a pupil center is not limited thereto, another method may satisfactorily adopted. For example, a pupil center may satisfactorily be defined based on a gravity of a pupil. The obtained pupil position relative to a corneal shape is also stored in the memory 55b.

On the contrary, in the case of measuring an eye refractive power (it is referred to as "an objective eye refractive power" hereinbelow), the operator changes the mode to the mode for measuring an eye refractive power (in the case of the continuous measurement mode, it is automatically changed to the mode for measuring an eye refractive power), then the measurement is performed by the measuring optical system 100. The refractive power calculating part 52 obtains distribution of an objective eye refractive power, based on each phase difference of each output signal from each photo-detector of the photo-receiving part 14. More specifically, firstly, the preliminary measurement is performed by a similar method of measuring a refractive power in the prior art, such as a phase difference method. Based on its result, the eye E is fogged by moving the lens 33. Thereafter, the center of each photo-detector 15a–15f is determined in a meridian direction where the photo-detectors 15a–15f are placed. This determination is based on each signal outputted from the photo-detectors 15g and 15h, the signals varying in accordance with movement of a slit-light (a slit-image) on the photo-receiving part 14. Next, based on a phase difference between each signal outputted from each photo-detector 15a–15f relative to the center of each photo-detector 15a–15f, each refractive power at each corneal part corresponding to each photo-detector is calculated. If this calculation is performed in order to obtain each refractive power per every meridian of each axial step under the condition that the projecting optical system 1 and the photo-receiving part 14 are made to be rotated 180° around the optical axis at a given angle, such as 1°, then the distribution of refractive power varying in a meridian direction can be obtained (in details, see Japanese Patent Publications Laid-Open No. HEI10(1998)-108836 and No. HEI10(1998)-108837 corresponding to U.S. Pat. No. 5,907,388). Where, the value of the refractive power is expressed as a vertex power (the apparatus can also output or convert a value of a refractive power as a spectacles power which is based on a position where a pair of spectacles is worn). The obtained distribution data of the objective eye refractive power is stored in a HDD 55a or the memory 55b.

If respective measured data including a corneal radius of curvature and an objective eye refractive power are obtained as above described, then the operator operates a keyboard 58 and/or a mouse 57 in accordance with an instruction displayed on a color display 56, connected to a control part 50, thereby causing analysis to start. The analysis part 54 provided for the control part 50 converts the corneal radius of curvature into a corneal refractive power, then executing an analysis program in order to obtain relationship between the converted corneal refractive power and the corresponding objective eye refractive power.

Next, a method of converting the corneal radius of curvature into the corneal refractive power. The corneal refractive power is such power that is obtained when a light parallel to an optical axis is refracted on the cornea. And the refracted light intersects with optical axis. The corneal refractive power is defined as the reciprocal of the distance between the corneal vertex and the intersection. When converting a corneal radius of curvature into the corneal refractive power, the Snell's law (or it is called the law of refraction) is used. When converting the corneal radius of curvature into the corneal refractive power D, following expression can be used in order to calculate the vicinity of the measuring optical axis (the vicinity of a corneal center) because of its little error:

$$D=(ne-1)/r,$$

where, r is defined as a corneal radius of curvature, ne is an equivalent refractive rate (in general, ne=1.3375).

However, the expression can be applied only to the vicinity of the measuring optical axis. If the expression is applied to the corneal periphery part (which is) far from the vicinity, then the error will increase. In the case of discussing the periphery part of the cornea, the refractive power according to the Snell's law is appropriate. The refractive power obtained under this definition is comparable with the objective eye refractive power under the same scale. In addition, the Snell's law defines that a normal line at an incident point of a light beam and a light beam refracted at this incident point are on the same plane at the time when the light beam enters into a refraction plane, and further defines that a ratio of a sin value of an angle formed by a normal line and an incident light beam and a sin value of an angle formed by a normal line and a refracted light beam is a constant. The Snell's law is given by following expression:

$$N \sin i = N' \sin i',$$

where, each refractive index at each medium of a refraction plane is defined as N and N', an angle formed by an incident light beam and a normal line is defined as i, and an angle formed by a refracted light beam and a normal line is defined as i'.

Figure 5:
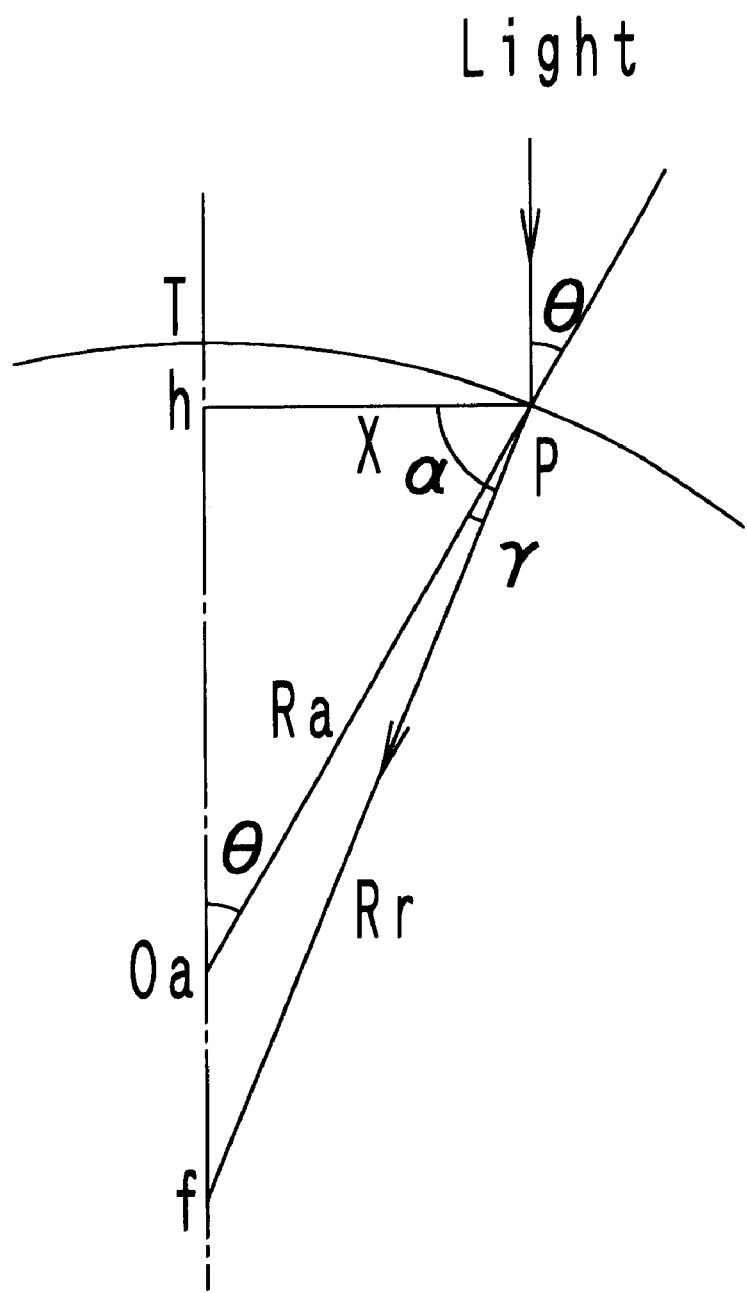
FIG. 5 is a view for illustrating a method of calculating a corneal refractive power.

Next, the calculation of the corneal refractive power by using the Snell's law will be described hereinafter. In FIG. 5, a light parallel to a line passing through a corneal vertex T and a curvature center Oa is defined as to refract at a point P on the cornea at a distance X from the corneal vertex T, and is defined as to intersect at a point f with a line TOa. Where, following definition is given (a unit of a distance is a meter):

Ra: a corneal radius of curvature at a point P
Rr: a distance from a point P to a point f
θ: an angle between a normal line at a point P and an incident light
γ: an angle between a normal line at a point P and a refracted light.

A refractive power at a point P can be calculated by following calculation steps.

Firstly, as shown in FIG. 5, the angle θ is given by following expression:

$$\theta = \sin^{-1}\left(\frac{X}{R_a}\right) \quad (1)$$

Next, the angle γ is given by following expression based on the Snell's law:

$$\gamma = \sin^{-1}\left(\frac{X}{R_a \times n}\right) \quad (2)$$

Based on the expressions (1) and (2), an angle α (an angle formed by a segment hP and a segment Pf), a distance Rr, and a segment hf are given by following expressions:

$$\alpha = 90 - \theta + \gamma$$

$$R_r = \frac{X}{\cos(\alpha)} \quad (3)$$

$$\overline{hf} = \sqrt{R_r^2 - X^2}$$

In addition, a distance of a segment Th is given by following expression:

$$\overline{Th} = R_a - \sqrt{R_a^2 - X^2} \quad (4)$$

Accordingly, a distance from the corneal vertex T to the point f is given by following expression:

$$\overline{Tf} = \overline{Th} + \overline{hf} = R_a - \sqrt{R_a^2 - X^2} + \sqrt{R_r^2 - X^2} \quad (5)$$

A refractive power DC in a cornea is given by following expression:

$$Dc = \frac{1}{\overline{Tf}} = \frac{1}{R_a - \sqrt{R_a^2 - X^2} + \sqrt{R_r^2 - X^2}} \quad (6)$$

In contrast, a refractive power D in air is given by following expression under definition that a refractive index is n (=1.376):

$$D = n \times Dc = \frac{n}{R_a - \sqrt{R_a^2 - X^2} + \sqrt{R_r^2 - X^2}} \quad (7)$$

If the calculation by using the above identified expressions (1) to (7) is performed with respect to all measuring region, then the corneal refractive power is calculated. Alternatively, the calculation may satisfactorily be performed by the corneal shape calculating part 53.

Next, the objective eye refractive power is then converted to a refractive power equivalent to a corneal surface with respect to the corneal refractive power calculated as described above. The converted value results in the form of a corneal refractive power necessary for causing the eye E to be emmetropia (in this specification, this is referred to as "an equivalent emmetropia corneal refractive power").

Figure 6:
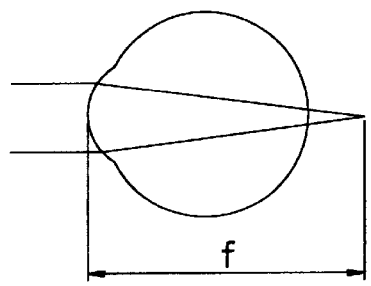
FIG. 6 is a view showing difference between a calculated value of a corneal refractive power obtained by measuring a corneal shape and a measured value obtained by an objective eye refractive power measurement.
Figure 6:
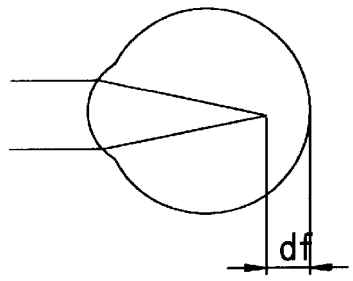

Herein, the relationship between the corneal refractive power obtained from a corneal shape and the objective eye refractive power is as following. As shown in FIG. 6, the meanings of a value of the corneal refractive power differs entirely from a value of the objective eye refractive power. The corneal refractive power is obtained by calculating a focal distance f, then converting it into the refractive power. In contrast, the objective eye refractive power is obtained by measuring a refractive power (correcting amount) df necessary for causing the eye to be emmetropia. For example, if the corneal refractive power obtained from a corneal shape is 43.50 D that is in the same measuring region as an objective eye refractive power, and the objective eye refractive power measured is 0 D, then it is indicated that the eye E has such optical system that forms an image on a retina when the corneal refractive power is 43.50 D. If the corneal refractive power is 43.50 D and the objective eye refractive power is −2 D, then it is indicated that the eye E is in need of correction of the corneal refractive power of an amount of −2 D (to be 41.50 D) so as to form an image on the retina.

Accordingly, in the region where the objective eye refractive power is measured, a corneal refractive power which causes the eye to be emmetropia is calculated in a manner of adding the measured objective eye refractive power including a sign to the corneal refractive power obtained from the corneal shape measurement. The calculated value proves to be the equivalent emmetropia corneal refractive power, given by following expression:

Equivalent emmetropia corneal refractive power = Corneal refractive power + Objective eye refractive power In addition, the equivalent emmetropia corneal refractive power can be converted into the corneal radius of curvature, based on the Snell's law. This conversion can be performed by using the below identified two expressions found by the same way as shown in FIG. 5:

$$R_r = \frac{R_a}{\sqrt{1 - \left(\frac{X}{n \times R_a}\right)^2 - \frac{1}{n}\sqrt{1 - \left(\frac{X}{R_a}\right)^2}}} \quad (8)$$

$$\sqrt{R_r^2 - X^2} + R_a - \sqrt{R_a^2 - X^2} - \frac{n}{D} = 0$$

Where, D is defined as the equivalent emmetropia corneal refractive power; Ra is the solved corneal radius of curvature.

By using the equivalent emmetropia corneal refractive power D and the corneal radius of curvature Ra converted, the relationship between the value of the objective eye refractive power and the value of the corneal radius of curvature obtained from the corneal shape measurement and the value of the corneal refractive power can be expressed in the form of the corneal surface. Thereby, the relationship can be utilized for estimating the corneal surface shape. In general, it is said that a total refractive power of an eye is a sum of a corneal refractive power and a lens refractive power, but it is not easy to know a lens refractive power. Additionally, an ocular axial length is also a cause of ametropia. In contrast, the above identified expressions enables the operator to understand relationship with a real corneal surface shape by a manner of replacing ametropia with a corneal surface shape, even if the operator does not know unknown values, such as a lens refractive power, an ocular axial length and the like.

Figure 7:
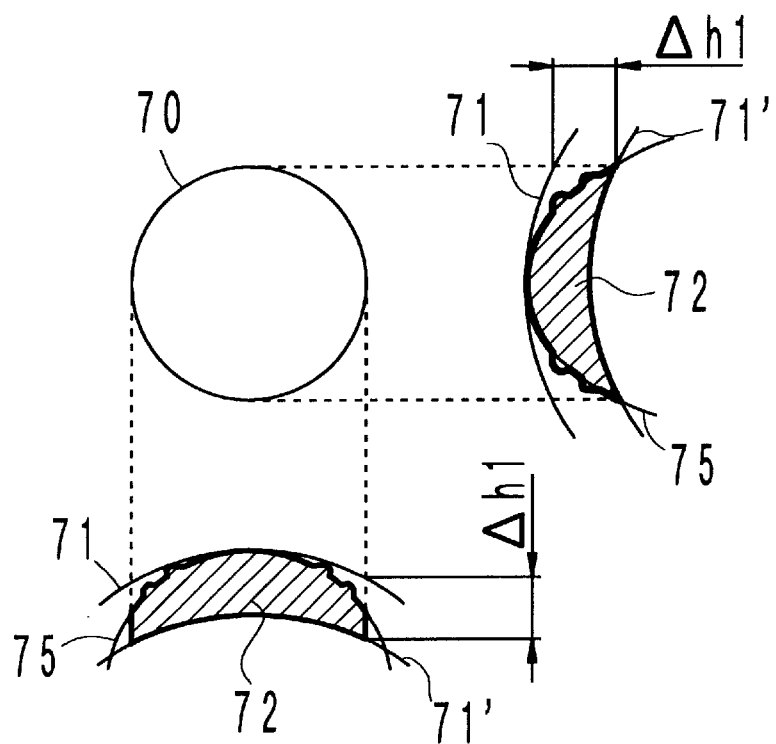
FIG. 7 is a view for illustrating a method of calculating an amount of corneal ablation.
Figure 7:
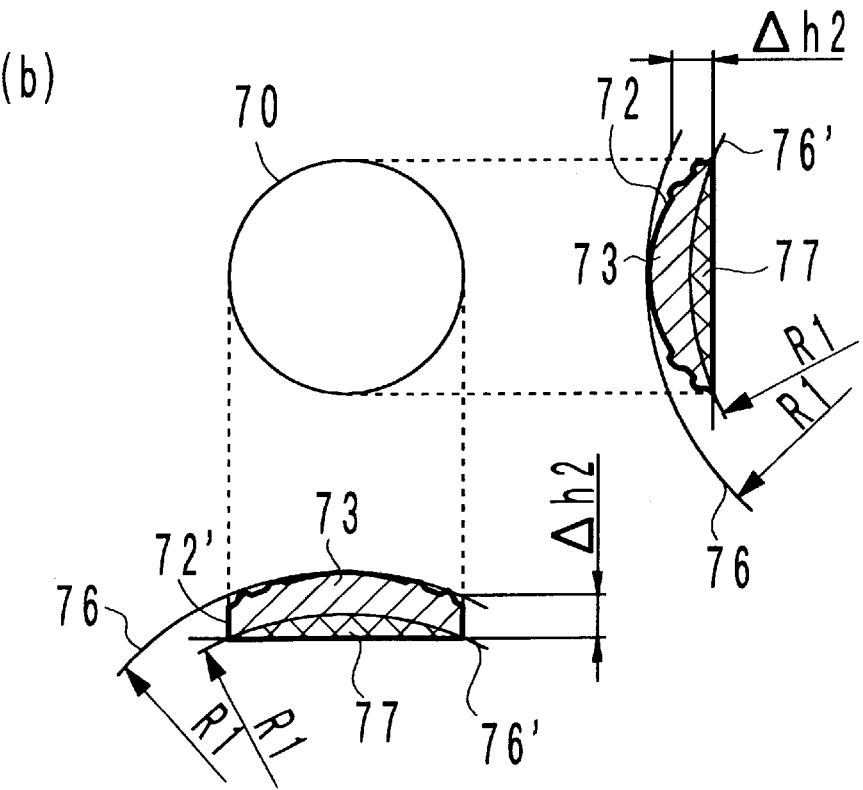
Figure 8:
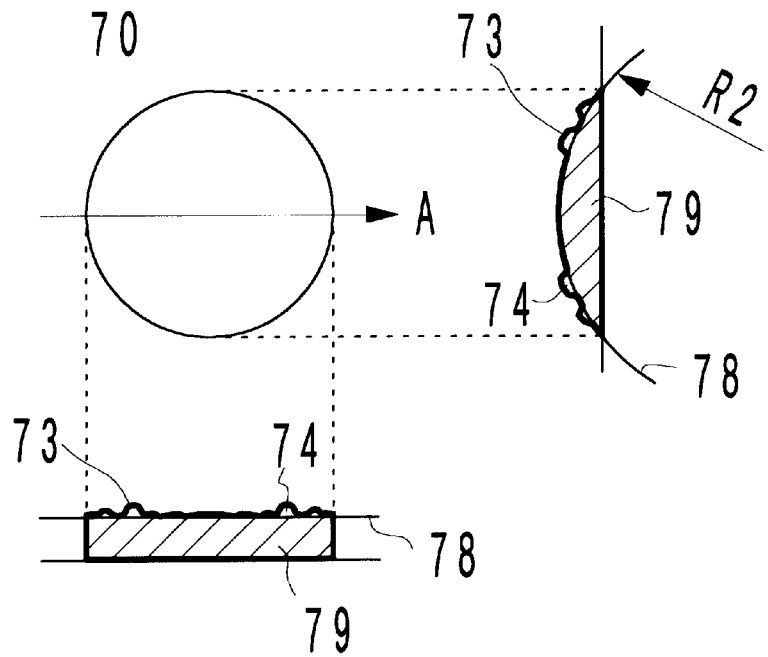
FIG. 8 is a view for illustrating a method of calculating an amount of corneal ablation.
Figure 8:
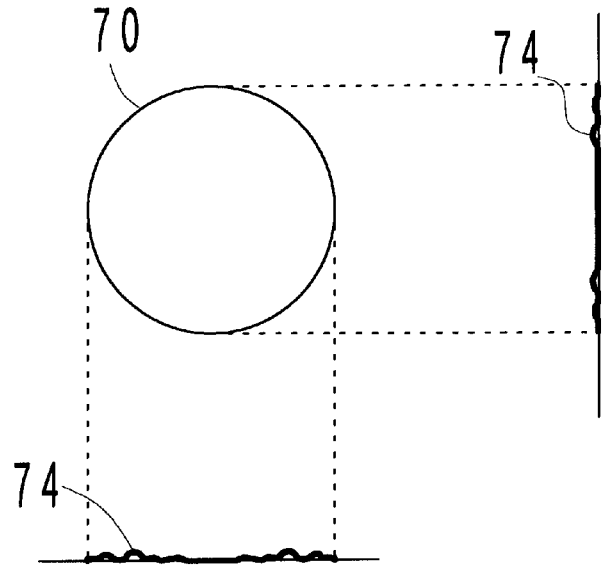
Figure 9:
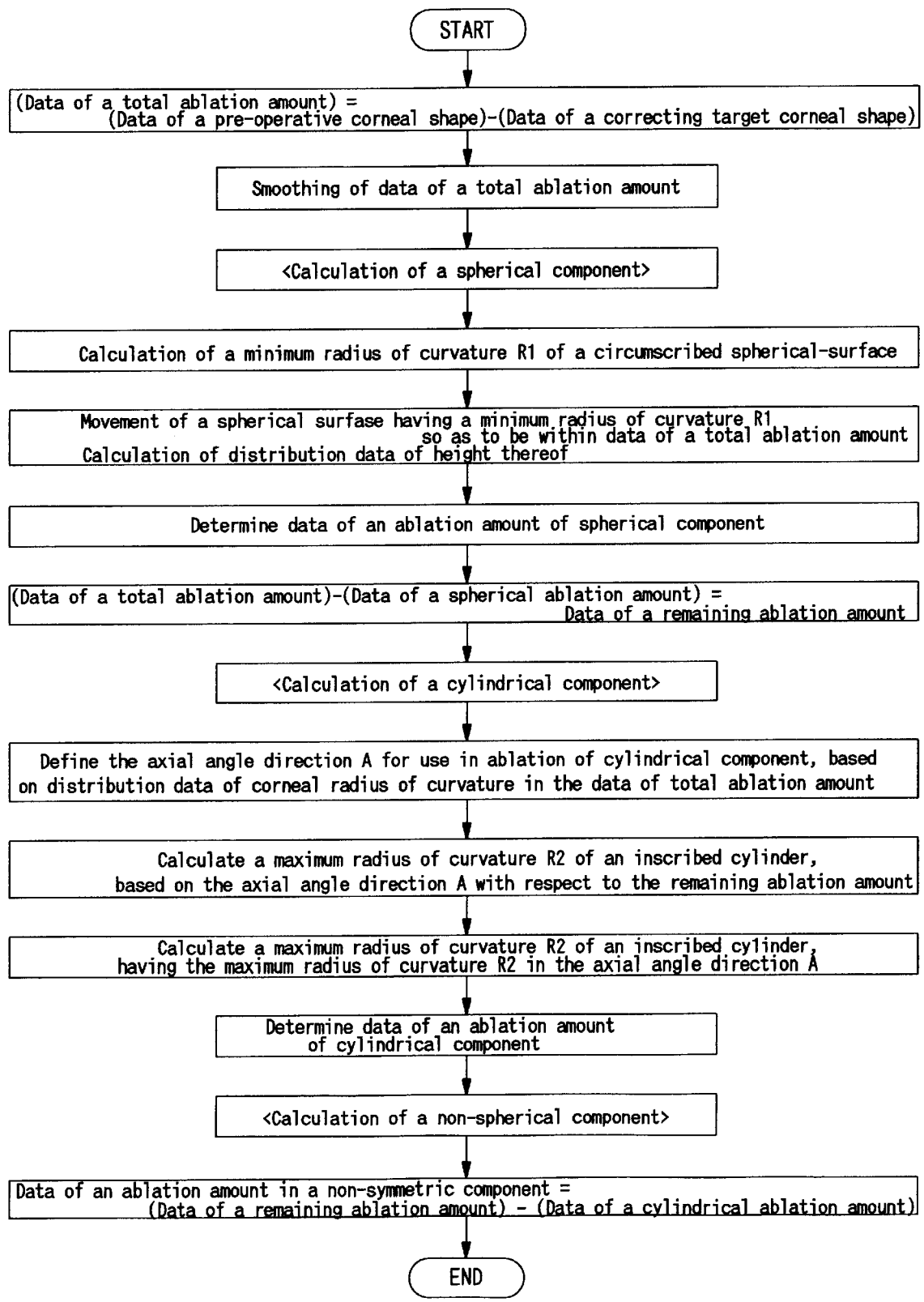
FIG. 9 is a flow chart showing a method of calculating an amount of corneal ablation.

Next, analysis of ablation data for use in surgical operation for correcting ametropia will be described hereinafter. By operating the mouse 57 and the like, the operator instructs the unit to execute an analysis program, then an analysis part 54 calculates data of ablation based on the corneal radius of curvature obtained from the corneal shape measurement and the corneal radius of curvature obtained by converting the equivalent emmetropia corneal refractive power. This calculation method will be described hereinafter, making a point of correcting myopia with referring to FIG. 7 and FIG. 8. FIG. 9 is a flow chart showing a calculation method.

Based on the corneal radius of curvature obtained by the corneal shape measurement, data of a pre-operative corneal shape is found as a three-dimensional shape. Based on the corneal radius of curvature obtained by converting the equivalent emmetropia corneal refractive power, data of a post-operative corneal shape (to be a target for correcting) is found. Subsequently, based on the difference between two data, data of a total ablation amount is calculated. That is, as shown in FIG. 7(a), data of a corneal shape 71 is made to be shifted a maximum amount Δh1 downward relative to the data of a pre-operative corneal shape 75 (resulting in data of a corneal shape 71'). Where, the data of a corneal shape 71 is a target for correcting and the maximum amount Δh1 is a difference in a range of an optical zone 70 which is an ablation region. Distribution data of height obtained by shifting is defined as data of a total ablation amount 72, and is obtained as data of a three-dimensional shape 72' of height distribution, as shown in FIG. 7(b). The data of an ablation amount at the moment may preferably be processed by smoothing.

In the case that an equivalent emmetropia corneal refractive power is not used as similar to the preferred embodiment of the present invention, distribution of data of an ablation amount can be obtained by eliminating the data of a post-operative corneal shape from the data of a pre-operative corneal corneal shape. Where, the data of a pre-operative corneal shape is found by the corneal shape measurement, and the data of a post-operative corneal shape is the estimation data, found by the data of a corrected refractive power (defined based on a refractive power obtained by a subjective eye refractive power measurement).

After obtaining the data of a total ablation amount 72, data of an ablation amount in a spherical component is calculated. For example, a minimum radius of curvature R1 of a spherical shape 76 is found. Where, the spherical shape 76 is circumscribed about a three-dimensional shape 72' of the data of a total ablation amount 72 (see FIG. 7(b)). The spherical shape 76 having the minimum radius of curvature R1 is made to be shifted Δh2 downward so as to stay in the data of a three-dimensional shape 72'0 (a spherical shape 76'). Distribution data of height obtained by shifting is defined as data of an ablation amount in a spherical surface 77. FIG. 8(a) shows data of a remaining ablation amount 73 obtained by subtracting the data of an ablation amount in a spherical surface 77 from the data of a total ablation amount 72 (the data of a three-dimensional shape 72'). Subsequently, data of an ablation amount in a cylindrical component is calculated based on the data of a remaining ablation amount 73.

Prior to calculate the data of an ablation amount in a cylindrical component, an axial direction angle A is defined following below mentioned procedures. Firstly, distribution data of a corneal radius of curvature at each coordinate position is established by using a shape of the data of a total ablation amount 72. Then, the flattest curvature direction is found among the established data and is defined as the axial angle direction A. In FIG. 8(a), the axial angle direction A is defined as 0°.

Next, a maximum radius of curvature R2 of a cylindrical shape 78 is found. Where, the cylindrical shape 78 is inscribed in a shape of the data of a remaining ablation amount 73, with defining the axial angle direction A, as shown in FIG. 8(a). Distribution data of height of the cylindrical shape 78 having the maximum radius of curvature R2 is defined as data of an ablation amount in a cylindrical surface 79. FIG. 8(b) shows data of a remainder obtained by subtracting the data of an ablation amount in a cylindrical surface 79 from the data of a remaining ablation amount 73. The remainder is defined as data of an ablation amount in an irregular astigmatism component (an asymmetric component) 74.

Above description is made adopting the case of myopia correction as an example, but the preferred embodiment is not limited thereto. Based on the aforementioned procedures, also in the case of hyperopia correction, data of an ablation amount in a spherical component and cylindrical component can be found so as to have such shape that an ablation amount of a periphery part is more than that of a center part.

In addition, above described procedure is an example of a method for calculating an ablation amount in a symmetric component and that in an asymmetric component. Thus, the ablation amount can be obtained various kinds of methods. For example, the astigmatism axial angle direction A is obtained as above mentioned, subsequently, in order to obtain the shape data of a total ablation, each sectional shape is found by analyzing per 2 μm, then each inscribed circle based on the axial angle direction A is found for each obtained sectional shape. Thereby, a spherical component and/or a non-spherical component can be found and each ablation amount thereof can be found. Furthermore, a remainder obtained by subtracting a spherical component and/or a non-spherical component in rotation symmetry, a cylindrical component in line symmetry, and the like, from the total ablation amount can be calculated and defined as an ablation amount in an asymmetric component.

As described above, an ablation amount in a spherical component (a non-spherical component), an ablation amount in a cylindrical component, and an ablation amount in an irregular astigmatism component are respectively obtained, then these data are outputted and displayed on a color display 56 graphically so as to be compared easily and visually with the distribution of an objective eye refractive power and the distribution of a corneal refractive power.

Figure 10:
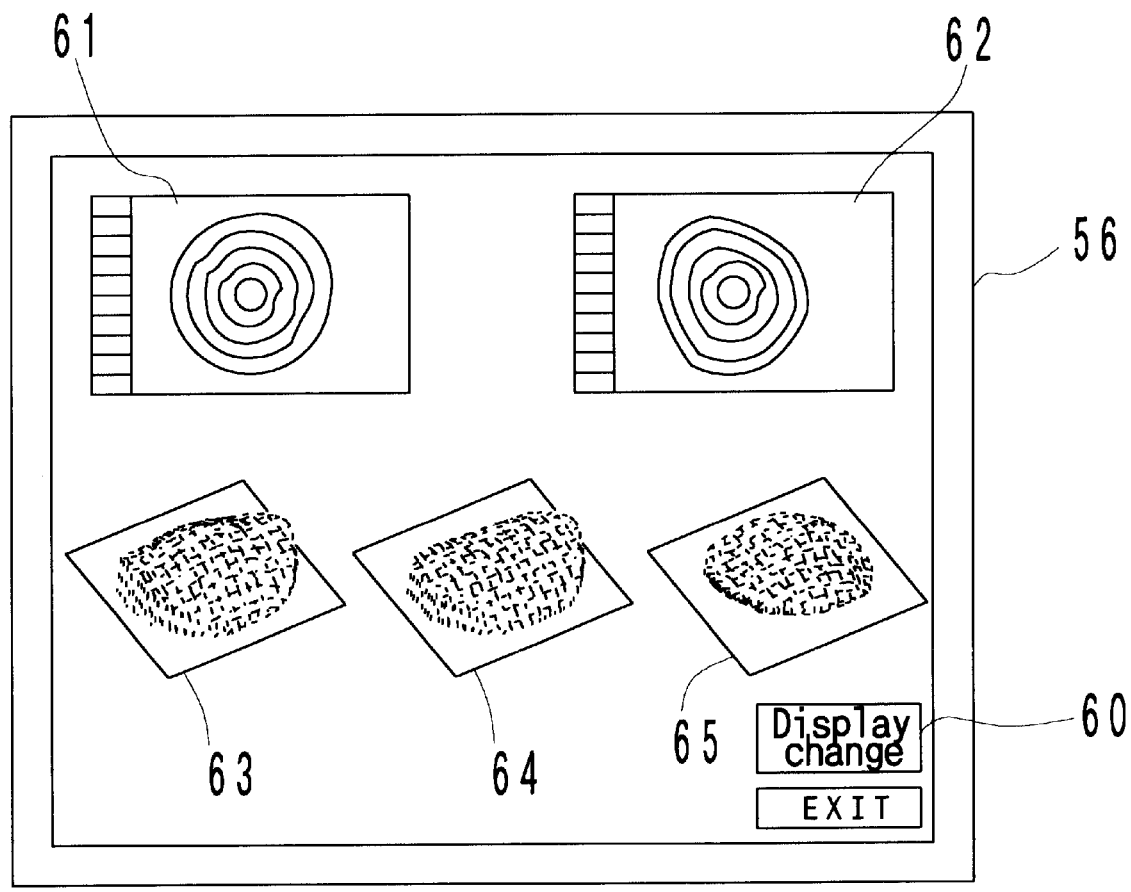
FIG. 10 is a view showing an example of a color map and a three-dimensional graphic display with respect to the distribution of refractive power and the distribution of ablation amount.

FIG. 10 is a view showing an example of a color map and a three-dimensional graphic display with respect to the distribution of a refractive power and the distribution of an ablation amount. The distribution of a corneal refractive power which is to be a target for correcting is displayed by way of a color map on a display part 62 at a right-upper part in the screen display; the distribution of a pre-operative corneal refractive power is displayed by way of a color map on a display part 61 at a left-upper part in the screen display. Furthermore, the distribution of a total ablation amount is displayed on a display part 63 at a left-lower part in the screen display as a three-dimensional shape; the distribution of an ablation amount in a symmetric component, such as a cylindrical component, on a display part 64 at a center-lower part in the screen display as a three-dimensional shape; the distribution of an ablation amount in a non-symmetric component, such as an irregular astigmatism component, is displayed on a display part 65 at a right-lower part in the screen display as a three-dimensional shape. In addition, the distribution of an ablation amount in a symmetric component (an asymmetric component) can be also displayed graphically similar to as mentioned above. Furthermore, a method of displaying can be changed each other among a color map display, a three-dimensional display and a display of a sectional (profile) image in a certain meridian direction, by using a change-over switch 60 provided at a right-lower part in the screen display.

As is described, the relation among the corneal shape measurement results, the objective eye refractive power measurement results, the data of a total ablation amount based on the above-mentioned results, the data of an ablation amount in a spherical (non-spherical) component, the data of an ablation amount in a cylindrical component, and the data of an ablation amount in an irregular astigmatism component is individually and respectively displayed graphically. Accordingly, in the case of the corneal correction surgery for treating the patient's eye so as to be emmetropia condition, the operator can understand visually what component of the ocular aberration should be ablated by the laser irradiation.

In the case that a maximum ablation amount excesses an allowance amount of corneal ablation with respect to all over the optical zone 70, an ablation amount is corrected so as to be within a range of an allowance amount by making the optical zone 70 small.

Following each data calculated by the analysis part 54, such as data of an ablation amount in a spherical (non-spherical) component, data of an ablation amount in a cylindrical component, and data of an ablation amount in an irregular astigmatism component is stored into HDD 55a and/or the memory 55b. These data are transferred to the surgical apparatus for a cornea 90, which ablates a cornea with an excimer laser beam via a communication cable, connected to a communication port 59b and FDD 59c driven by the floppy disc drive (FDD) 59a. Position of a pupil center with respect to the above identified data is also transferred to and stored into the surgical apparatus for a cornea 90. The surgical apparatus for a cornea 90 determines a number of irradiation pulses and an irradiation power on each coordinates of the cornea of the patient's eye, based on the inputted data of an corneal ablation amount. In accordance with the determined values, the surgical apparatus for a cornea 90 carries out surgery for operating upon a cornea Ec by controlling a laser irradiation.

Examples of the surgical apparatus for a cornea 90 are disclosed by Japanese Patent Publication Laid-Open No. HEI9(1997)-122167 (corresponding to U.S. Pat. No 5,800, 424) and Japanese Patent Publication Laid-Open No. HEI9 (1997)-266925 (corresponding to U.S. Pat. No. 5,906,608).

Figure 11:
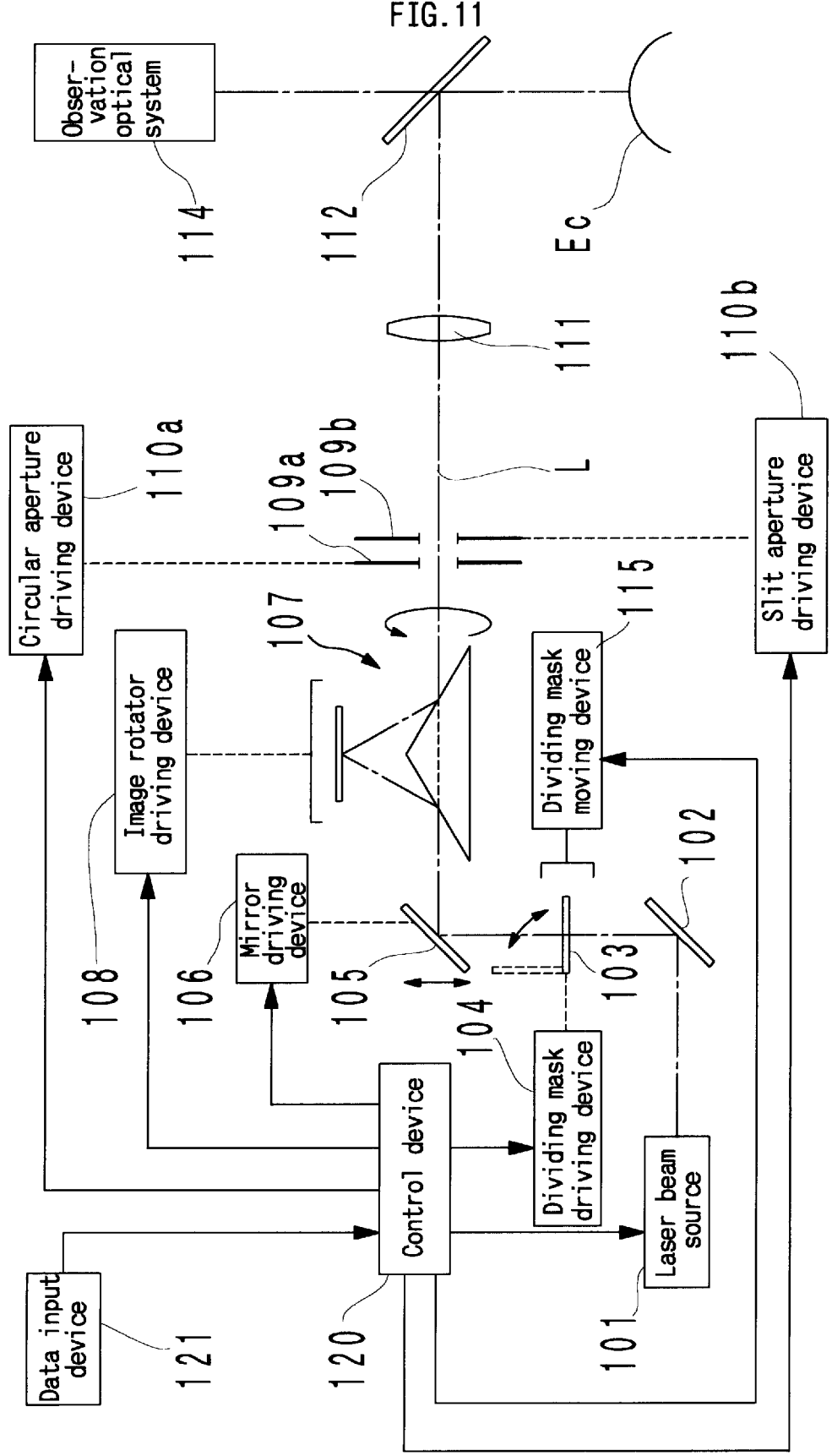
FIG. 11 is a view showing a schematic arrangement of an optical system and a control system in the surgical apparatus for a cornea of the preferred embodiment of the present invention.

FIG. 11 is a view showing a schematic arrangement of an optical system and a control system provided for the surgical apparatus for a cornea 90. 101 is an excimer laser beam source, and 102 is a reflecting mirror. 103 is a dividing mask having a plurality of strip-shaped masks which form a line. The strip shaped-masks are shut and opened by a dividing mask driving unit 104, thereby a long direction of an excimer laser beam in the form of a thin rectangle shape, from a laser beam source 101, is partially cut. A laser beam passing through the mask 103 is scanned by a plane mirror 105, thereby the laser beam is moved (shifted). 107 is an image rotator, and 109a is a circular aperture having a variable opening. 109b is a slit aperture having a variable opening, more specifically, an opening width thereof is controlled by a slit aperture driving unit 110b, and a direction of the slit opening is rotated about an optical axis L. 111 is a projecting lens, 112 is a dichloic mirror for reflecting an excimer laser beam and for making a visible light pass through, and 114 is an observation optical system. 121 is a data input unit, and 120 is a control unit for controlling respective driving units.

Next, the corneal surgery operation by using the surgical apparatus for a cornea 90 will be described hereinbelow. Firstly, the data of a corneal ablation amount and the data of a pupil center position, obtained by using the apparatus for determining an amount of corneal ablation, are inputted by an input unit 121. Subsequently, a pupil center is found in order to define an origin of an eye where should be a standard position for the surgical operation. Similar to the procedures as in the above-mentioned apparatus for determining an amount of corneal ablation, the procedure for defining the pupil center is performed based on an anterior portion image photographed by CCD camera (not shown) in the observation optical system 114. In this procedure, the pupil center may satisfactorily defined as such an intersecting point that is defined by following first and second lines: the first line is passing through a center between two points and extending in a perpendicular direction (the two points are respectively on opposite edges of a pupil, the points on edges are the intersecting points with a horizontal line passing through approximately a center of an pupil); and the second line is passing through a center between two points and extending in a horizontal direction (the two points are respectively on opposite edges of a pupil, the points on edges are intersecting points with a perpendicular line passing through approximately a center of a pupil). Or the pupil center may satisfactorily defined based on a gravity of the pupil. Other than these methods, the operator may observes the pupil with an operation microscope, then may simply define the pupil center. Subsequently, the control device 120 causes the pupil center position with respect to the data of a corneal ablation amount sent by the apparatus for defining an amount of corneal ablation, to coincide with the pupil center position defined by the above mentioned surgical apparatus for a cornea 90. Then, the control device 120 performs ablation based on the data of an ablation amount in a spherical (non-spherical) component, the data of an ablation amount in a cylindrical component, the data of an ablation amount in an irregular astigmatism component, as following.

In the case of correcting myopia on a spherical (non-spherical) surface based on the data of an ablation amount in a spherical (non-spherical) component, a laser beam is limited by the circular aperture 109a, then a plane mirror 105 is caused to move in turn so that the laser beam may move to the Gaussian distribution direction. Every time when the laser beam finishes moving on one surface (one scan), then the image rotator 107 rotates and causes the laser beam to change its moving direction (for example, three directions at intervals of 120°). Then, the region limited by the circular aperture 109a is ablated by the laser beam approximately uniformly. If this ablation is performed every time when changing an opening region of the circular aperture 109a in turn, then the ablation can be performed with respect to a spherical (non-spherical) component so that the center part of a cornea may be ablated deeply and the periphery part of a cornea may be ablated slightly.

In the case of correcting astigmatism, based on the data of an ablation amount in a cylindrical component, a size of an opening region of the circular aperture 109a is fixed in accordance with the optical zone, while, an opening width of the slit aperture 109b is caused to vary. The slit aperture 109b is adjusted in advance by using the driving device 110b so that an opening width of the slit may vary in a direction of a strong major principal meridian. Concerning the laser beam irradiation as similar to the case of above-mentioned myopia correction, the laser beam is moved by causing a plane mirror 105 to move in turn so that the laser beam may move to the Gaussian distribution direction. Then, every time when scanning a laser beam once, the image rotator 107 rotates, thus changing a moving direction of the laser beam. Thereby, the region limited by the slit aperture 109b is ablated approximately uniformly. This ablation is performed repeatedly, under the condition that an opening width of the slit aperture 109b is caused to vary in turn. Accordingly, the ablation for a cylindrical component can be performed.

The ablation in an irregular astigmatism component is performed as following, with the state that the dividing mask 103 is disposed on an optical path. The plane mirror 105 is caused to move in turn, therefore, a laser beam emitted to the cornea Ec is caused to move to such a direction (the Gaussian distribution direction) that is perpendicular to a long direction of its rectangular shape. Simultaneously, if a strip-shaped mask of the dividing mask 103 is selectively opened and/or shut, then the cornea Ec becomes to be irradiated with such a laser beam only for a small region that passes through an opened part of the mask. Based on the data of an ablation amount in an irregular astigmatism component, opening and/or shutting of the dividing mask 103 is controlled at each moving position of the laser beam which is moved by the plane mirror 105, and the the dividing mask 103 is slightly moved in a long direction of the beam via a mask moving device 115. In addition, an ablation amount for each position is adjusted by controlling a period of time for irradiation. Accordingly, the ablation for an irregular astigmatism component can be performed.

As described above, the ablation in a symmetric component (the ablation in a spherical (non-spherical) component, the ablation in a cylindrical component) and the ablation in a non-symmetric component are respectively and separately performed. Accordingly, a period of time necessary for surgery can be shortened, and the operation can be performed efficiently.

In the preferred embodiment, the ablation in a spherical (non-spherical) component, the ablation in a cylindrical component and the ablation in a non-symmetric component is performed in that order, however, the order is not limited thereto, so the order may satisfactorily be changed voluntarily.

Furthermore, in the preferred embodiment, the description is made, as an example, based on the surgical apparatus for a cornea, which performs ablation by way of controlling an aperture and/or a dividing mask. Other than this surgical apparatus, the present invention can be applied to such apparatus that scans a laser beam of a small spot, by a manner of two-dimensional scanning. In the case of this kind of apparatus, the stage for ablating a symmetric component may satisfactorily be separated from the stage for ablating an asymmetric component. Because the scanning of a laser beam can be controlled easily, so the ablation can be performed accurately.

Furthermore, in the preferred embodiment, the apparatus (the apparatus for determining an amount of corneal ablation) of the present invention comprises following all mechanisms in one body: the mechanism for measuring a corneal shape (a corneal radius of curvature); the mechanism for measuring an eye objective refractive power; the mechanism for calculating data of a corneal shape which is used as a target for correcting, based on results measured by above-mentioned two mechanisms; and the mechanism for calculating a corneal ablation amount, based on the data of a pre-operative corneal shape and the data of a correcting-target corneal shape. However, these mechanisms may satisfactorily be provided for separate devices individually or, some of which may satisfactorily combined and provided for each device. The apparatus for determining an amount of corneal ablation may satisfactorily be such apparatus that calculates data of a corneal ablation amount by simply inputting data of a pre-operative corneal shape and data of a correcting-target corneal shape. As described above, various modifications and variations are possible for the present invention.

Industrial Applicability

As described above, according to the present invention, even in the case of an irregular astigmatism or the like, an appropriate amount of corneal ablation can be determined in accordance with a corneal shape and/or a refractive power of the eye to be operated, for the purpose of performing surgical operation for correcting ametropia adequately.

In the case, the ablation may preferably be performed by the surgical apparatus for a cornea in a manner of separating ablation for a symmetric component and ablation for an asymmetric component on the basis of the determined amount of corneal ablation. Accordingly, a period of time necessary for whole operation may be shortened, and the operation may be performed efficiently and easily.

What is claimed is:

1. An apparatus for determining an amount of corneal ablation, based on which surgical operation for correcting ametropia is performed, the apparatus comprising:

a first input unit for inputting data of a pre-operative corneal shape of a patient's eye;

a second input unit for inputting data of a post-operative corneal shape of the eye, to be estimated;

an ablation amount calculating unit for calculating data of a corneal ablation amount of the eye, in a manner of calculating data of an ablation amount in a symmetric component and data of an ablation amount in an a symmetric component separately and respectively, based on the data inputted by the first input unit and the second input unit; and an output unit for outputting results calculated by the ablation amount calculating unit.

2. The apparatus according to claim 1, wherein the output unit comprises a display unit for displaying the results calculated by the ablation amount calculating unit, graphically.

3. The apparatus according to claim 1, wherein the output unit comprises a sending unit for sending the results calculated by the ablation amount calculating unit, to a surgical apparatus for a cornea.

4. The apparatus according to claim 1, wherein the ablation amount calculating unit calculates at least one data selected from the group consisting of a spherical component, a non-spherical component, and a cylindrical component, for use as the data of the ablation amount in the symmetric component.

5. The apparatus according to claim 1, further comprising a corneal shape measuring unit for measuring distribution data of a corneal radius of curvature of the eye; wherein the first input unit inputs pre-operative distribution data measured by the corneal shape measuring unit into the ablation amount calculating unit.

6. The apparatus according to claim 1, further comprising:

a corneal shape measuring unit for measuring distribution data of a corneal radius of curvature of the eye;

an eye refractive power measuring unit for measuring distribution data of an eye refractive power of the eye;

a corneal shape calculating unit for calculating distribution data of an equivalent emmetropia corneal refractive power of the eye based on pre-operative distribution data measured by the corneal shape measuring unit and pre-operative distribution data measured by the eye refractive power measuring unit, subsequently, calculating distribution data of a post-operative corneal radius of curvature of the eye, to be estimated, based on the obtained distribution data of the equivalent emmetropia corneal refractive power; wherein the first input unit inputs the results measured by the corneal shape measuring unit into the ablation amount calculating unit, and the second input unit inputs the results obtained by the corneal shape calculating unit into the ablation amount calculating unit.

7. The apparatus according to claim 6, wherein the corneal shape calculating unit calculates distribution data of a corneal refractive power based on the distribution data of the corneal radius of curvature measured by the corneal shape measuring unit, subsequently, calculating the distribution data of the equivalent emmetropia corneal refractive power based on the obtained distribution data of the corneal refractive power an d the distribution data of the eye refractive power measured by the eye refractive power measuring unit; and the output unit includes a display unit for displaying graphically at least one distribution data selected from the group consisting of the distribution data of the corneal refractive power, the distribution data of the eye refractive power and the distribution data of the equivalent emmetropia corneal refractive power.

8. The apparatus according to claim 1, further comprising:

a correcting-refractive power input unit for inputting data of a correcting-refractive power of the eye; and a corneal shape calculating unit for calculating the data of a post-operative corneal shape, to be estimated, based on the inputted data of the correcting-refractive power;

wherein the second input unit inputs the results calculated by the corneal shape calculating unit into the ablation amount calculating unit.

9. The apparatus according to claim 1, wherein at least one between the first input unit and the second input unit comprises an input unit with which an operator inputs data.

10. A surgical apparatus for a cornea, which corrects ametropia by ablating a cornea of a patient's eye with a laser beam, the apparatus comprising:

a first input unit for inputting data of a pre-operative corneal shape of the eye;

a second input unit for inputting data of a post-operative corneal shape of the eye, to be estimated;

an ablation amount calculating unit for calculating data of a corneal ablation amount of the eye, in a manner of calculating data of an ablation amount in a symmetric component and data of an ablation amount in an a symmetric component separately and respectively, based on the data inputted by the first input unit and the second input unit;

a first ablation unit for ablating the cornea, based on the obtained data of the ablation amount in the symmetric component; and a second ablation unit for ablating the cornea, based on the obtained data of the ablation amount in the asymmetric component.

11. The surgical apparatus for a cornea, according to claim 10, wherein the first ablation unit comprises an irradiating optical system for irradiating the cornea with the laser beam from a laser source; and the second ablation unit shares the irradiating optical system with the first ablation unit.

12. The surgical apparatus for a cornea, according to claim 11, wherein the second ablation unit comprises a beam dividing unit for dividing the laser beam, the beam dividing unit being disposed on a light path of the irradiating optical system.

13. An apparatus for determining an amount of corneal ablation, based on which surgical operation for correcting ametropia is performed, the apparatus comprising:

a corneal shape measuring unit for measuring distribution data of a corneal radius of curvature of a patient's eye;

an eye refractive power measuring unit for measuring distribution data of an eye refractive power of the eye;

a corneal shape calculating unit for calculating distribution data of an equivalent emmetropia corneal refractive power of the eye based on pre-operative distribution data measured by the corneal shape measuring unit and pre-operative distribution data measured by the eye refractive power measuring unit, subsequently, calculating distribution data of a post-operative corneal radius of curvature of the eye, to be estimated, based on the obtained distribution data of the equivalent emmetropia corneal refractive power;

an ablation amount calculating unit for calculating data of a corneal ablation amount of the eye, in a manner of calculating data of an ablation amount in a symmetric component and data of an ablation amount in an asymmetric component separately and respectively, based on the results measured by the corneal shape measuring unit and the results calculated by the corneal shape calculating unit; and an output unit for outputting results calculated by the ablation amount calculating unit.

14. The apparatus according to claim 13, wherein the corneal shape calculating unit calculates distribution data of a corneal refractive power based on the distribution data of the corneal radius of curvature measured by the corneal shape measuring unit, subsequently, calculating the distribution data of the equivalent emmetropia corneal refractive power based on the obtained distribution data of the corneal refractive power and the distribution data of the eye refractive power measured by the eye refractive power measuring unit; and the output unit includes a display unit for displaying graphically at least one data selected from the group consisting of the distribution data of the corneal refractive power, the distribution data of the eye refractive power, the distribution data of the equivalent emmetropia corneal refractive power, data of a total ablation amount, data of the ablation amount in the symmetric component and data of the ablation amount in the asymmetric component.

15. The apparatus according to claim 13, wherein the output unit comprises a sending unit for sending the results calculated by the ablation amount calculating unit, to a surgical apparatus for a cornea.

* * * * *

UNITED STATES PATENT AND TRADEMARK OFFICE
CERTIFICATE OF CORRECTION

PATENT NO. : 6,467,907 B1
DATED : October 22, 2002
INVENTOR(S) : Masanao Fujieda et al.

It is certified that error appears in the above-identified patent and that said Letters Patent is hereby corrected as shown below:

Title page,
Item [57], ABSTRACT,
Line 3, "calculates" should read -- calculate --.

Column 16, line 67 to column 17, line 1,
"a symmetric" should read -- asymmetric --.

Column 17,
Line 54, "an d" should read -- and --.

Column 18,
Lines 17-18, "a symmetric" should read -- asymmetric --.

Signed and Sealed this

Twenty-fifth Day of February, 2003

JAMES E. ROGAN
*Director of the United States Patent and Trademark Office*